United States Patent
Simon et al.

(10) Patent No.: US 8,598,397 B2
(45) Date of Patent: Dec. 3, 2013

(54) METHOD FOR THE TREATMENT OF A SMALL-AND/OR MEDIUM-PORE ZEOLITE AND USE THEREOF IN THE OLIGOMERISATION OF LIGHT OLEFINS

(75) Inventors: Laurent Simon, Lyons (FR); Sylvie Lacombe, Saint Genis Laval (FR)

(73) Assignee: IFP Energies nouvelles, Rueil Malmaison Cedex (FR)

( * ) Notice: Subject to any disclaimer, the term of this patent is extended or adjusted under 35 U.S.C. 154(b) by 1072 days.

(21) Appl. No.: 11/993,996

(22) PCT Filed: Jun. 22, 2006

(86) PCT No.: PCT/FR2006/001427
§ 371 (c)(1),
(2), (4) Date: Dec. 27, 2007

(87) PCT Pub. No.: WO2007/003737
PCT Pub. Date: Jan. 11, 2007

(65) Prior Publication Data
US 2008/0139860 A1   Jun. 12, 2008

(30) Foreign Application Priority Data
Jun. 28, 2005 (FR) ..................... 05 06588

(51) Int. Cl.
*C07C 2/12* (2006.01)
*B01J 29/18* (2006.01)

(52) U.S. Cl.
USPC ........... 585/533; 585/520; 585/530; 585/532; 502/64; 502/71; 502/78; 502/85; 502/86

(58) Field of Classification Search
USPC ............ 502/64; 423/325, 335, 336, 713, 714; 585/520, 530, 533, 532; 505/64, 71, 505/78, 85, 86
See application file for complete search history.

(56) References Cited

U.S. PATENT DOCUMENTS

| | | | | |
|---|---|---|---|---|
| 4,876,411 A | * | 10/1989 | Bowes et al. | 585/533 |
| 4,996,034 A | * | 2/1991 | Skeels | 423/713 |
| 5,057,640 A | * | 10/1991 | Chang et al. | 585/533 |
| 5,080,878 A | * | 1/1992 | Bowes et al. | 423/713 |
| 5,157,191 A | * | 10/1992 | Bowes et al. | 585/533 |
| 5,567,666 A | * | 10/1996 | Beck et al. | 502/71 |
| 5,672,800 A | | 9/1997 | Mathys et al. | |
| 2005/0020435 A1 | * | 1/2005 | Beck et al. | 502/63 |
| 2006/0217580 A1 | * | 9/2006 | Kuechler et al. | 585/533 |
| 2006/0287565 A1 | | 12/2006 | Du Toit | |
| 2007/0255081 A1 | | 11/2007 | Beadle et al. | |

FOREIGN PATENT DOCUMENTS

| | | |
|---|---|---|
| EP | 0 493 931 A | 7/1992 |
| EP | 0 757 976 A | 2/1997 |
| FR | 2 477 903 A | 9/1981 |
| WO | WO 02/04575 A | 1/2002 |
| WO | WO 2005/058777 A | 6/2005 |
| WO | WO 2005058777 A1 * | 6/2005 |

* cited by examiner

*Primary Examiner* — In Suk Bullock
*Assistant Examiner* — Bradley Etherton
(74) *Attorney, Agent, or Firm* — Millen, White, Zelano & Branigan, P.C.

(57) ABSTRACT

Described is a process for the treatment of at least one zeolite having a pore size of less than or equal to 7 Å comprising at least a) a step for dealumination of said zeolite, b) a cationic exchange step using at least one cation other than $H^+$, c) a step for treatment of said zeolite obtained in step b) in the presence of at least one molecular compound containing at least one silicon atom, and d) at least one heat treatment step. The present invention also concerns the preparation of a catalyst containing the zeolite treated in accordance with the treatment process the subject-matter of the invention and the use of said catalyst in a process for the oligomerization of an olefinic charge containing hydrocarbon molecules having from 2 to 12 carbon atoms per molecule.

18 Claims, No Drawings

METHOD FOR THE TREATMENT OF A SMALL-AND/OR MEDIUM-PORE ZEOLITE AND USE THEREOF IN THE OLIGOMERISATION OF LIGHT OLEFINS

TECHNICAL FIELD

The present invention relates to a process for the treatment of at least one zeolite having small and/or medium pores, in particular pores of a size less than or equal to 7 Å in order to obtain a modified zeolite which is advantageously used in a catalyst and employed in different chemical hydrocarbon conversion processes. More particularly the invention relates to the use of a catalyst containing the modified zeolite in a process for the oligomerisation of a light olefinic charge.

STATE OF THE ART

A number of patents have already set forth methods of modifying zeolites. In particular U.S. Pat. No. 4,402,867 describes a method of preparing a zeolite-based catalyst comprising a step which involves depositing in the aqueous phase at least 0.3% by weight of amorphous silica in the interior of the pores of the zeolite. U.S. Pat. No. 4,996,034 describes a process for substituting aluminium atoms present in a zeolite framework by silicon atoms, that process being carried out in a step in an aqueous medium using salts of fluorosilicates. U.S. Pat. No. 4,451,572 describes the preparation of a zeolitic catalyst comprising a step of depositing organosilicic materials in a vapour or liquid phase, the zeolites concerned being zeolites with large pores, in particular zeolite Y.

U.S. Pat. No. 5,057,640 describes a process for the oligomerisation of propylene using a catalyst containing a zeolite with an Si/Al ratio of greater than 12 and a constraint index (CI) of between 1 and 12 and in which at least 0.1% by weight of silica with respect to the weight of the zeolite was added. The catalyst referred to in U.S. Pat. No. 5,057,640 has an n-hexane adsorption of 1% less than on the starting zeolite.

SUMMARY

The present invention concerns a process for the treatment of at least one zeolite having a pore size of less than or equal to 7 Å comprising at least a) a step for dealumination of said zeolite, b) a cationic exchange step using at least one cation other than $H^+$, c) a step for treatment of said zeolite obtained in step b) in the presence of at least one molecular compound containing at least one silicon atom, and d) at least one heat treatment step. The zeolite is preferably selected from zeolites of structural type MEL, MFI, ITH, NES, EUO, ERI, FER, CHA, MFS, MWW, MTT, TON and MOR. It is preferred that the zeolite resulting from step b) is devoid of any proton in order to carry out step c) in the optimum fashion. Step c) of the process according to the invention is preferably implemented by proceeding to the deposit of the molecular compound containing at least one silicon atom in the gaseous phase and is performed in a fixed bed reactor.

The present invention also concerns the preparation of a catalyst containing the zeolite treated in accordance with the treatment process the subject-matter of the invention and the use of said catalyst in a process for the oligomerisation of an olefinic charge containing hydrocarbon molecules having from 2 to 12 carbon atoms per molecule.
Interest It was surprisingly discovered that a catalyst comprising a zeolite modified by a treatment process comprising at least a) a step for dealumination of said zeolite, b) a cationic exchange step using at least one cation other than $H^+$, c) a step for treatment of said zeolite obtained in step b) in the presence of at least one molecular compound containing at least one silicon atom, and d) at least one heat treatment step results in improved catalytic performances, in particular in terms of activity and selectivity in a reaction for the oligomerisation of an olefinic charge containing hydrocarbon molecules having from 2 to 12 carbon atoms per molecule, preferably from 3 to 7 carbon atoms per molecule, and highly preferably containing from 4 to 6 carbon atoms per molecule. In particular such a catalyst makes it possible to substantially increase the catalytic activity, thus leading to a noticeable increase in the level of conversion of the olefinic charge and an increase in the yields of the petrol and diesel cuts with respect to those obtained by employing a catalyst from the state of the art. The cetane number which denotes the linearity of the hydrocarbon chains present in diesel is also advantageously improved in comparison with that which a diesel cut generally has. The use of the catalyst as described hereinbefore in a process for oligomerisation of an olefinic charge containing hydrocarbon molecules having from 2 to 12 carbon atoms per molecule, preferably from 3 to 7 carbon atoms per molecule, and highly preferably containing from 4 to 6 carbon atoms per molecule makes it possible to produce an oligomerate of very high quality which can advantageously be directly integrated in the gas oil pool of a refinery.

DESCRIPTION OF THE INVENTION

The present invention concerns a process for the treatment of at least one zeolite having a pore size of less than or equal to 7 Å comprising at least:
  a) a step for dealumination of said zeolite,
  b) a cationic exchange step using at least one cation other than $H^+$,
  c) a step for treatment of said zeolite obtained in step, b) in the presence of at least one molecular compound containing at least one silicon atom, and
  d) at least one heat treatment step.

In accordance with the invention the zeolites treated in accordance with the process of the invention have a pore size of less than or equal to 7 Å and preferably less than 6.5 Å. The zeolites are those defined in the classification "Atlas of Zeolite Structure Types", W. M Meier, D. H. Olson and Ch. Baerlocher, 5th revised edition, 2001, Elsevier" to which the present application also refers but they may also be any zeolite having a pore size of less than or equal to 7 Å. The zeolites listed in the "Atlas of Zeolite Structure Types" are classified therein in accordance with the size of their openings of pores or passages. All the zeolites having a pore size of less than or equal to 7 Å and preferably less than 6.5 Å are suitable for carrying out the treatment process according to the invention. Advantageously the zeolite to be treated in accordance with the process of the invention has either at least passages, the opening of which is defined by a ring with 8 oxygen atoms (8 MR) or at least passages, the opening of which is defined by a ring with 10 oxygen atoms (10 MR), or once again both passages, the opening of which is defined by a ring with 8 oxygen atoms (8 MR) and passages, the opening of which is defined by a ring with 10 oxygen atoms (10 MR), which passages can be interconnected. A zeolite having at least passages of which the opening is defined by a ring with 12 oxygen atoms (12 MR) is also suitable for carrying out the process of the invention since it has a pore size of less than or equal to 7 Å. In particular a zeolite of structural type MOR which has both passages of which the opening is defined by a ring with 8 oxygen atoms (8 MR) and passages of which the opening is defined by a ring with 12 oxygen atoms (12 MR) is suitable for carrying out the treatment process according to the invention.

The zeolite to be treated with the process of the invention contains at least silicon and aluminium in a proportion such that the Si/Al atomic ratio is preferably between 2 and 200, more preferably between 5 and 100 and still more preferably between 8 and 80. It advantageously contains at least one other element W which is different from the silicon and the aluminium, being integrated in tetrahedric form in the framework of the zeolite. Preferably said element W is selected from iron, germanium, boron and titanium and represents a portion by weight of between 5 and 30% of all of the constituent atoms of the zeolite framework other than the oxygen atoms. The zeolite then has a (Si+W)/Al ratio of between 2 and 200, preferably between 5 and 100 and highly preferably between 8 and 80, W being defined as hereinbefore.

The zeolite to be treated by the process according to the invention is preferably selected from the zeolites of structural type MEL, MFI, ITH, NES, EUO, ERI, FER, CHA, MFS, MWW, MTT, TON and MOR and highly preferably said zeolite is selected from zeolites of structural type TON, MFS, MOR and FER. Among the zeolites of structural type MEL the zeolite ZSM-11 is preferred. Among the zeolites of structural type MFI the zeolite ZSM-5 is preferred. Among the zeolites of structural type ITH the zeolite ITQ-13 is preferred (U.S. Pat. No. 6,471,941). Among the zeolites of structural type NES the zeolite NU-87 is preferred. Among the zeolites of structural type EUO the zeolite EU-1 is preferred. Among the zeolites of structural type ERI the zeolite erionite is preferred. Among the zeolites of structural type FER the zeolites ferrierite and ZSM-35 are preferred. Among the zeolites of structural type CHA the zeolite chabazite is preferred. Among the zeolites of structural type MFS the zeolite ZSM-57 is preferred. Among the zeolites of structural type MWW the zeolite MCM-22 is preferred. Among the zeolites of structural type MTT the zeolite ZSM-23 is preferred. Among the zeolites of structural type TON the zeolite ZSM-22 is preferred. Among the zeolites of structural type MOR the zeolite mordenite is preferred. Those zeolites and the manner of preparation thereof are well known to the man skilled in the art.

Step a) of the process of the invention is a dealumination step which consists of partially extracting aluminium atoms from the zeolite framework. Preferably the Si/Al atomic ratio of the dealuminated zeolite obtained at the outcome of the step a) is increased by at least 10% in comparison with the initial Si/Al atomic ratio of the zeolite to be treated in accordance with the process of the invention and highly preferably said step a) of the process of the invention leads to an increase by at least 20% in the initial Si/Al atomic ratio of the zeolite to be treated in accordance with the process of the invention.

The dealumination step a) of the process of the invention can be carried out by any method known to the man skilled in the art. Advantageously it is implemented by one or other of the two methods described hereinafter, the first dealumination method being referred to as the acid attack method and the second dealumination method being referred to as the heat treatment method.

Prior to carrying out step a) the zeolite to be treated in accordance with the process of the invention can be either in its rough synthesis form still containing the organic structuring agent used for preparing it or in calcined form. Very preferably it is in calcined form and contains at least one cation, preferably a proton, in such a way that it is in its protoned form (in hydrogen $H^+$ form) in which the sodium content is less than 0.2% by weight, preferably less than 0.1% by weight and highly preferably less than 0.05% by weight with respect to the total weight of dry zeolite. To obtain a zeolite in its protoned form, prior to carrying out step a), the procedure generally involves one or more ion exchange operations using a solution containing at least one ammonium salt, for example ammonium nitrate $NH_4HO_3$ in such a way as to at least partially and preferably practically totally eliminate an alkali metal cation present in the zeolite. The aim of a calcination step in a flow of dry air at a temperature which is generally between about 400 and 500° C. is then to regenerate the protons of the zeolite by ammonia desorption thus leading to the hydrogen form of the zeolite.

A first method of carrying out step a) of the process of the invention is the method referred to as direct acid attack. It is preferably applied when the zeolite to be dealuminated is in its hydrogen $H^+$ form and is freed of organic structuring agent. That method comprises a treatment step using an aqueous solution of an inorganic acid such as $HNO_3$ or $HCl$ or an organic acid such as $CH_3CO_2H$. That step can be repeated as many times as necessary to achieve the desired level of dealumination. To achieve the desired Si/Al ratio it is necessary to choose the operating conditions well: from that point of view the most critical parameters are the temperature for the treatment by the acid aqueous solution which is advantageously between 25° C. and 100° C., the concentration of that acid which is advantageously between 1N and 15N, the nature of that acid which is preferably selected from $HNO_3$, $HCl$ and $CH_3CO_2H$, the ratio between the amount of acid solution and the volume of zeolite treated which is preferably between 1 and 30, the treatment duration which is preferably between 30 minutes and 10 hours and the number of treatments carried out which is preferably between 1 and 5.

It is also possible to effect dealumination treatments using dealuminating chemical compounds such as by way of examples and without being an exhaustive list, sodium tetrachloride ($SiCl_4$) (Sohn et al., Applied Catalysis A—General, 218 (1-2), 229-234 (2001), ammonium hexafluorosilicate (($NH_4)_2SiF_6$) (Garralon et al., Zeolites, 8, 268-272 (1988)), ethylenediaminetetracetic acid (EDTA) (Gola et al., Microporous and Mesoporous Materials, 40 (1-3), 73-83 (2000)), as well as its mono- and disodium form. Those reactants can be used in solution or in the gaseous phase for example in the case of $SiCl_4$.

A second method of carrying out step a) of the process of the invention is the method referred to as the heat treatment method (in particular using steam or "steaming"). That method comprises at least one framework dealumination cycle which involves at least one heat treatment carried out at a temperature which is generally between 550 and 900° C. in the presence of a carrier gas, preferably nitrogen and in the presence or absence of oxygen. That heat treatment is preferably carried out in the presence of steam and is advantageously followed by at least one acid attack using an aqueous solution of an inorganic acid such as $HNO_3$ or $HCl$ or an organic acid such as $CH_3CO_2H$. During the heat treatment the carrier gas may preferably contain between 10 and 90% and very preferably between 20 and 80% of steam. The duration of the heat treatment which is preferably carried out in the presence of steam is advantageously between 1 and 10 hours and highly advantageously between 1 hour and 7 hours. The conditions of the acid attack which advantageously follows the heat treatment are so adapted as to achieve the desired level of dealumination. The aqueous acid solution treatment temperature is preferably between 25° C. and 100° C., the concentration of that acid is preferably between 1N and 15N, the acid is advantageously selected from $HNO_3$, $HCl$ or $CH_3CO_2H$, the ratio between the amount of acid solution and the volume of zeolite treated is preferably between 1 and 30, the treatment duration involved in the acid attack is preferably between 30 minutes and 10 hours and the number of acid attack treatments performed is preferably between 1 and 5. For the same purpose it is also possible to adjust the number of heat treatment-acid attack dealumination cycles which are carried out.

This second method of performing step a) of the process of the invention is applied for dealuminating a rough synthesis zeolite still containing the organic structuring agent and for dealuminating a zeolite in its calcinated form in which it is freed of the organic structuring agent. In particular when the situation involves carrying out said step a) on a zeolite which still contains the organic structuring agent, the heat treatment which is advantageously effected at a temperature which is generally between 550° C. and 900° C. and preferably carried out in the presence of steam permits simultaneous calcination of the organic structuring agent.

A variant of that second method involves replacing the optional acid attack step, that is to say the treatment by an acid solution, by a treatment using a solution of a chemical dealuminating compound such as for example sodium tetrachloride ($SiCl_4$) (Sohn et al., Applied Catalysis A—General, 218 (1-2), 229-234 (2001), ammonium hexafluorosilicate (($NH_4)_2$ $SiF_6$) (Garralon et al., Zeolites, 8, 268-272 (1988)), ethylenediaminetetracetic acid (EDTA) (Gola et al., Microporous and Mesoporous Materials, 40 (1-3), 73-83 (2000)), as well as its mono- and disodium form. Those reactants can be used in solution or in the gaseous phase for example in the case of $SiCl_4$.

The cycle for dealumination of the framework comprising at least one heat treatment step preferably carried out in the presence of steam and preferably followed by at least one attack step in an acid medium on the zeolite can be repeated as many times as is necessary to obtain the dealuminated zeolite having the desired characteristics, in particular in terms of the Si/Al atomic ratio. Likewise, following the heat treatment which is preferably carried out in the presence of steam, a plurality of successive acid attack operations using acid solutions of possibly different levels of concentration can be implemented.

At the outcome of the dealumination step a) of the process according to the invention the dealuminated zeolite is in cationic form, preferably in protoned form (hydrogen $H^+$ form) and is freed of the organic structuring agent. The cation present in the dealuminated zeolite at the end of step a) is a cation referred to as a compensation cation as is well known to the man skilled in the art.

The dealuminated zeolite in cationic form, preferably in protoned form, is then subjected, in accordance with step b) of the process of the invention, to a cationic exchange step using at least one cation other than $H^+$. Preferably this is a non-acid cation. The cationic exchange in step b) of the process according to the invention can be implemented by all the procedures known to the man skilled in the art and in particular by excess solution exchange. The cation employed to carry out that cationic exchange with the compensation cation can be of any type and of any volume in order to make it possible to obtain different textural characteristics for the final zeolite. The preferred cation for carrying out the step b) is selected from the metals of groups IA and IIA of the periodic table of elements and more particularly that cation is selected from the cations $Na^+$, $Li^+$, $K^+$, $Rb^+$, $Cs^+$, $Ba^{2+}$ and $Ca^{2+}$. It is also advantageous in regard to carrying out the process of the invention to exchange the compensation cation by an ammonium ion $NH_4^+$. The zeolite obtained at the end of step b) of the process of the invention is an exchanged zeolite. The exchange rate with respect to the proton is higher than 95%.

The exchanged zeolite produced in step b) and preferably devoid of any cation $H^+$ is ready to undergo selectivation in respect of acidity of its internal and external surfaces. In accordance with the present invention the term "selectivation" is used to denote neutralisation of the acidity of the external surface and the internal surface of each of the crystals of the zeolite. Neutralisation of acidity can be effected by any method known to the man skilled in the art. The conventional methods, for implementing selectivation of zeolites, generally use molecules of which the kinetic diameter is less than the diameter of the opening of the pores of the dealuminated zeolite.

The molecules generally used for passivating or selectivating the external and internal surfaces of the zeolite are compounds containing atoms which can interact with the external and internal surface sites of each of the crystals of the zeolite. The molecules used are organic or inorganic molecules containing one or more silicon atoms. Thus, in accordance with step c) of the treatment process according to the invention, the zeolite which is exchanged in accordance with step b) of the process of the invention is subjected to a treatment step in the presence of at least one molecular compound containing at least one silicon atom. That step c) makes it possible to deposit a layer of amorphous silica on the external and internal surfaces of each of the crystals of the zeolite, resulting in at least partial and preferably complete reduction in the Lewis acidity. Lewis acidity is characterised by infrared with the adsorption of CO. Integration of the band between 2230 and 2143 $cm^{-1}$ makes it possible to demonstrate the variation in Lewis acidity on the zeolite prior to and after the treatment in accordance with step c) of the process of the invention. The loss in Lewis acidity is greater than 30%. The molecular compound used in that step c) preferably comprises at most 2 silicon atoms per molecule. Preferably the molecular compound containing at least one silicon atom is selected from the compounds of the formula Si—$R_4$ and $Si_2$-$R_6$ in which R can be either hydrogen or an alkyl, aryl or acyl group, or an alkoxy group (O—R') or a hydroxyl group (—OH) or a halogen. The group R can be either identical or different within the same molecule Si—$R_4$ or $Si_2$-$R_6$. For example in accordance with the formulae set out hereinbefore it will be possible to choose molecular compounds of the formulae $SiH_4$, $Si_2H_6$ or $Si(C_2H_5)_3(CH_3)$. Thus the molecular compound containing at least one silicon atom employed in step c) of the process of the invention may a compound of silane, disilane, alkylsilane, alkoxysilane or siloxane type. That molecular compound involves a kinetic diameter of less than the diameter of the opening of the pores of the dealuminated zeolite.

The step c) of the process of the invention which involves treating the exchanged zeolite produced in step b) in the presence of at least one molecular compound containing at least one silicon atom is effected by deposit of said compound on the internal and external surfaces of the zeolite. It is possible to implement a deposit in the gaseous phase, referred to as CVD ("chemical vapour deposition") or a deposit in the liquid phase, referred to as CLD ("chemical liquid deposition"), using all the methods known to the man skilled in the art. Preferably the step c) is carried out by implementing deposit of the molecular compound containing at least one silicon atom in the gaseous phase.

A CLD deposition procedure can be effected either in an aqueous medium or in an organic solvent. Upon impregnation in an aqueous medium of the molecular compound containing at least one silicon atom, one or more surface-active agents may or may not be added to the impregnation solution. CLD deposition is well known to the man skilled in the art (Chon et al., Studies Surface Science and Catalysis, vol. 105. 2059-2065, 1997).

Preferably deposit of the molecular compound containing at least one silicon atom on the internal and external surfaces of the zeolite is carried out in the gaseous phase. Step c) of the process of the invention is carried out in a fixed bed reactor. Prior to the gaseous phase deposition reaction (CVD) in the fixed bed reactor the zeolite is preferably activated. Activation of the zeolite in the fixed bed reactor is carried out in oxygen, air or inert gas, or in a mixture of air and inert gas or oxygen and inert gas. The zeolite activation temperature is advantageously between 100 and 600° C. and highly advantageously between 200° C. and 550° C. The molecular compound containing at least one silicon atom which is to be deposited on the internal and external surfaces of each of the crystals of the zeolite is passed into the reactor in the vapour phase, the molecular compound being diluted in a carrier gas which may be either hydrogen ($H_2$), air, argon (Ar), helium (He), or again nitrogen ($N_2$), the carrier gas preferably being an inert gas selected from Ar, He and $N_2$. To obtain a layer of amorphous silica of optimum quality on the internal and external surfaces of the zeolite it is necessary to choose the operating conditions well for deposit of the molecular compound containing at least one silicon atom. In particular the temperature of the zeolite bed during the deposition procedure is preferably between 10° C. and 300° C. and very preferably between 25 and 200° C., the partial pressure in the gaseous phase of the molecular compound to be deposited on the internal and external surfaces of the zeolite is preferably between 0.0001 and 0.5 bar and very preferably between 0.001 and 0.2 bar, the duration of the deposition procedure is preferably between 10 minutes and 10 hours and very preferably between 30 minutes and 5 hours and still more preferably between 1 hour and 3 hours.

In accordance with step d) of the process of the invention the molecular compound containing at least one silicon atom is decomposed by a heat treatment which is carried out at a temperature which is preferably between 200 and 700° C., more preferably between 300 and 500° C. That heat treatment step is carried out in air, oxygen, hydrogen, nitrogen or argon, or in a mixture of nitrogen and argon, which step can optionally be carried out in the presence of steam. The duration of that treatment is advantageously between 2 hours and 5 hours.

In the situation where cationic exchange step b) of the process of the invention is carried out with an ammonium cation $NH_4^+$ the step d) consisting of a heat treatment simultaneously implements decomposition of the molecular compound employed for carrying out step c) of the process of the invention and the production of the modified zeolite by the treatment of the process according to the invention, in its hydrogen form.

In the situation where the cationic exchange step b) of the process of the invention is carried out with a cation different from $H^+$, preferably selected from the metals of groups IA and IIA and different from $NH_4^+$ step d) of the process of the invention as described hereinbefore is followed by a step e) for exchange of said cation by an ammonium cation, the step e) itself being followed by a step f) involving a heat treatment.

Step e) comprises one or more ionic exchange operations carried out by a solution containing at least one ammonium salt, for example ammonium nitrate $NH_4NO_3$, in such a way as to at least partially and preferably practically totally and indeed totally eliminate the compensation cation which is still present in the zeolite resulting from step d) of the process of the invention and introduced in the course of step b) of the process of the invention. Step e) is followed by a step f) involving a heat treatment which is preferably carried out in a flow of dry air at a temperature which is advantageously between about 400 and 500° C. The aim of that step f) is to obtain the zeolite treated in accordance with the process of the invention in its hydrogen $H^+$ form by ammonia desorption.

The present invention also concerns a process for the preparation of a catalyst comprising a zeolite treated in accordance with the treatment process of the invention as described hereinbefore.

The preparation process comprises at least one step of shaping the treated zeolite with at least one matrix and possibly a binder. The matrix used is a mineral matrix which is porous, amorphous or poorly crystallised, of oxide type. It is selected from alumina, silica, silica-alumina, clays, in particular natural clays such as kaolin or bentonite, magnesia, titanium oxide, boron oxide, zirconia, aluminium phosphates, titanium phosphates, zirconium phosphates and carbon. It is also possible to select a matrix selected from aluminates. Preferably the matrix is an alumina in all its forms which are known to the man skilled in the art and preferably gamma alumina. The operation of shaping the treated zeolite with at least one matrix is generally such that the catalyst is in the form of extrudates which are cylindrical or polylobate such as bilobate, trilobate, polylobate of straight or twisted shape, but it may optionally be such that the catalyst is in the form of crushed powders, tablets, rings, balls or wheels. The conditions involved in shaping the treated zeolite, the choice of the matrix, optionally prior crushing of the zeolite, the peptisation process, the addition of porogenic agent, the mixing time, the extrusion pressure if the catalyst is shaped in the form of extrudates, the rate of drying and the drying time are determined for each matrix in accordance with the rules which are well known to the man skilled in the art.

The process for preparation of the catalyst according to the invention optionally comprises a step of depositing at least one metal, which is effected either prior to the shaping operation or when mixing the treated zeolite and the matrix or yet again after the shaping operation. The metal is preferably a metal selected from group VIII of the periodic table of elements and more preferably is nickel. The content by weight of that metal is advantageously between 1 and 5% with respect to the weight of the catalyst.

When the addition of at least one metal selected from group VIII is effected after the shaping operation, that metal can then be added either prior to calcination or preferably after calcination of the matrix-treated zeolite mixture. The added metal is generally deposited either practically totally on the zeolite or in part on the zeolite and in part on the matrix or preferably practically totally on the matrix, this being effected in a manner which is known to the man skilled in the art by a suitable choice of the parameters used in the deposition operation such as for example the nature of the precursor of that metal. The deposit of at least one metal in group VIII is generally effected by the procedure of dry impregnation, impregnation by excess or preferably by one or more ionic exchange operations.

By way of example one of the preferred methods of preparing the catalyst according to the invention comprises mixing at least the zeolite which has been treated in accordance with the treatment process of the invention in a moist matrix gel (generally obtained by mixing at least an acid and a matrix powder), for example alumina, for a period necessary to obtain good homogeneity of the paste which is obtained in that way, or for example for a period of around ten minutes, and then passing that paste through a die to form extrudates, for example of a diameter between 0.4 and 4 mm as inclusive limits, preferably between 0.4 and 2.5 mm as inclusive limits and preferably again between 0.8 and 2.0 mm as inclusive limits. Then, after drying for some hours at about 120° C. in a drying cabinet and after calcination, for example for a period of about 2 hours at about 400° C., the metal of group VIII is deposited, for example by ionic exchange in the presence of a competitor agent, the deposit operation being followed by calcination, for example for about 2 hours at about 400° C.

Another object of the invention is the use of the catalyst prepared by the process of the invention and comprising a zeolite modified by the treatment process of the invention, in chemical hydrocarbon conversion processes and in particular in a process for the oligomerisation of an olefinic charge containing hydrocarbon molecules having from 2 to 12 carbon atoms per molecule. Preferably the charge used for carrying out the oligomerisation process contains hydrocarbon molecules containing from 3 to 7 carbon atoms per molecule and very preferably containing from 4 to 6 carbon atoms per molecule. The charge employed in the oligomerisation process according to the invention contains from 20 to 100% by weight, preferably from 25 to 80% by weight and very preferably from 50 to 80% by weight of olefins, the linear olefins representing from 10 to 100% by weight, preferably from 15 to 95% and very preferably from 50 to 95% by weight of all of the olefins present in that charge.

Possible sources for the olefinic charge used in the oligomerisation process according to the invention are the light or cracking cut in a fluidised bed (fluid catalytic cracking or FCC), from a steam cracker and etherification unit effluents.

Preferably the charge used in the oligomerisation process is of Raffinat II type, that is to say a C4 cut containing more than 50% by weight of linear C4 olefins and less than 5% by weight of isobutene, or a C4 cut containing more than 30% by weight of linear olefins and less than 5% by weight of isobutene, for example resulting from a process for the production of MTBE or TAME or a process of type SELECTOPOL (registered trademark) or a C3/C4 cut resulting from a fluidised bed catalytic cracking process, that is to say a cut containing a propane/propylene mixture in a proportion by weight of about 5/25 and a butane/butene mixture in a proportion by weight of about 25/45.

The oligomerisation process is preferably carried out under the following operating conditions: the total pressure is between 0.1 and 10 MPa and preferably between 0.3 and 7 MPa, the temperature is between 40 and 600° C. and preferably between 60 and 400° C., and the spatial hourly velocity (VVH) is between 0.01 and 100 h$^{-1}$ and preferably between 0.4 and 30 h$^{-1}$.

It will be clearly specified that, in accordance with the invention, the oligomerisation process corresponds to an addition limited to essentially 2 to 6 monomers or base molecules, said monomers being olefins. Oligomerisation is considered as being "essentially linear" insofar as at least 75%, preferably at least 80% and still more preferably at least 90% of the oligomers obtained are linear.

The following examples illustrate the present invention without limiting the scope thereof.

EXAMPLES

Example 1 (Invention)

Treatment of a Zeolite of Structural Type FER

To effect dealumination of the zeolite H-FER, the procedure first involves a treatment of 100 g of that zeolite (Si/Al=10.2) for a period of 2 h at 600° C. in a flow of $N_2$ containing 60% by weight of $H_2O$. Then the resulting zeolite is subsequently treated twice with an aqueous solution of acid $HNO_3$ at a concentration of ION (volume solution/volume zeolite=5) under reflux for a period of 3 hours, washed twice with distilled water and then dried. After rinsing the zeolite is then exchanged using a solution of $NH_4NO_3$ under reflux for a period of 2 h and then dried. The exchanged zeolite is introduced into a fixed bed reactor where it is firstly subjected to activation in a flow of nitrogen at 200° C. The temperature of the reactor is then adjusted to 50° C. and then a partial pressure of 0.15 bar of $Si_2H_6$ is added in the flow of nitrogen. After 2 h of reaction the zeolite is stripped for 24 h at 120° C. to evacuate the non-reactive $Si_2H_6$. Decomposition of the molecular compound $Si_2H_6$ is effected in $N_2$ saturated in respect of $H_2O$ at 350° C. for 2 hours, then a thermal treatment in pure $N_2$ is effected at 450° C. for 2 hours. That results in a modified zeolite Zl (Si/Al=21.1) in protoned form, of structural type FER and comprising an amorphous silica layer on its external and internal surfaces.

The zeolite Z1 is then shaped by extrusion with an alumina gel so as to produce after drying at 120° C. and calcination at 450° C. in dry air, a catalyst which contains 60% by weight of zeolite Z1 and 40% by weight of alumina.

Example 2 (Invention)

Treatment of a Zeolite of Structural Type MFS

To effect dealumination of the zeolite Na-ZSM-57, the procedure first involves a treatment of 20 g of that zeolite (Si/Al=45.2) for a period of 2 h at 600° C. in a flow of $N_2$ containing 60% by weight of $H_2O$. Then the resulting zeolite is subsequently treated twice with an aqueous solution of acid $HNO_3$ at a concentration of ION (volume solution/volume zeolite=5) under reflux for a period of 3 hours, washed twice with distilled water and then dried. After rinsing the zeolite is then exchanged using a solution of $NaNO_3$ at 80° C. for a period of 2 h and then dried. The exchanged zeolite is introduced into a fixed bed reactor where it is firstly subjected to activation in a flow of nitrogen at 450° C. The temperature of the reactor is then adjusted to 50° C. and then a partial pressure of 0.15 bar of $Si_2H_6$ is added in the flow of nitrogen. After 2 h of reaction the zeolite is stripped for 24 h at 120° C. to evacuate the non-reactive $Si_2H_6$. Decomposition of the molecular compound $Si_2H_6$ is effected in $N_2$ saturated in respect of $H_2O$ at 350° C. for 2 hours. Finally the zeolite is exchanged using a solution of $NH_4NO_3$ under reflux for 2 h and then calcined at 450° C. for 2 h. That results in a modified zeolite Z2 (Si/Al=53.7) in protoned form, of structural type MFS comprising an amorphous silica layer on its external and internal surfaces.

The zeolite Z2 is then shaped by extrusion with an alumina gel so as to produce after drying at 120° C. and calcination at 450° C. in dry air, a catalyst which contains 60% by weight of zeolite Z2 and 40% by weight of alumina.

Example 3 (Invention)

Treatment of a Zeolite of Structural Type MOR

To effect dealumination of the zeolite H-MOR, the procedure first involves a treatment of 100 g of that zeolite (Si/Al=9.1) for a period of 2 h at 650° C. in a flow of $N_2$ containing 60% by weight of $H_2O$. Then the resulting zeolite is subsequently treated twice with an aqueous solution of acid $HNO_3$ at a concentration of 8N (volume solution/volume zeolite=5) under reflux for a period of 3 hours, washed twice with distilled water and then dried. After rinsing the zeolite is then exchanged using a solution of $NH_4NO_3$ under reflux for a period of 2 h and then dried. The exchanged zeolite is introduced into a fixed bed reactor where it is firstly subjected to activation in a flow of nitrogen at 200° C. The temperature of the reactor is then adjusted to 50° C. and then a partial pressure of 0.15 bar of $Si_2H_6$ is added in the flow of nitrogen. After 2 h of reaction the zeolite is stripped for 24 h at 120° C. to evacuate the non-reactive $Si_2H_6$. Decomposition of the molecular compound $Si_2H_6$ is effected in $N_2$ saturated in respect of $H_2O$ at 350° C. for 2 hours, then a thermal treatment in pure $N_2$ is effected at 450° C. for 2 hours. That results in a modified zeolite Z3 (Si/Al=25.4) in protoned form, of structural type MOR comprising an amorphous silica layer on its external and internal surfaces.

The zeolite Z3 is then shaped by extrusion with an alumina gel so as to produce after drying at 120° C. and calcination at 450° C. in dry air, a catalyst which contains 60% by weight of zeolite Z3 and 40% by weight of alumina.

Example 4 (Comparative)

Treatment of a Zeolite of Structural Type FER Without a Dealumination Step

The same treatment as that set forth in example 1 is carried out, with omission of the dealumination step.

An amount of 100 g of zeolite H-FER (Si/Al=10.2) was exchanged using a solution of $NH_4NO_3$ under reflux for a period of 2 h, and then dried. After activation of the exchanged zeolite in a flow of nitrogen in a fixed bed reactor at 200° C. the temperature of the reactor is adjusted to 50° C. and then a partial pressure of 0.15 bar of $Si_2H_6$ is added in the flow of nitrogen. After 2 h of reaction the zeolite is stripped for 24 h at 120° C. to evacuate the non-reactive $Si_2H_6$. Decomposition of the molecular compound $Si_2H_6$ is effected in $N_2$ saturated in respect of $H_2O$ at 350° C. for 2 h, then a heat treatment in pure $N_2$ is effected at 450° C. for 2 h. The result obtained in this way is a zeolite Z1d of structural type FER, which is not dealuminated, and comprising an amorphous silica layer on its external and internal surfaces.

The zeolite Z1d is then shaped by extrusion with an alumina gel so as to produce after drying at 120° C. and calcination at 450° C. in dry air, a catalyst which contains 60% by weight of zeolite Z1d and 40% by weight of alumina.

Example 5 (Comparative)

Treatment of a Zeolite of Structural Type MFS Without a Dealumination Step

The same treatment as that set forth in example 2 is carried out, with omission of the dealumination step.

An amount of 20 g of zeolite Na-ZSM (Si/Al=45.2), already in non-acid form, was activated in a flow of nitrogen in a fixed bed reactor at 450° C., then the temperature of the reactor is adjusted to 50° C. and a partial pressure of 0.15 bar of $Si_2H_6$ is added in the flow of nitrogen. After 2 h of reaction the zeolite is stripped for 24 h at 120° C. to evacuate the non-reactive $Si_2H_6$. Decomposition of the molecular compound $Si_2H_6$ is effected in $N_2$ saturated in respect of $H_2O$ at 350° C. for 2 h. Finally the zeolite is exchanged using a solution of $NH_4NO_3$ under reflux for 2 h and then calcined at 450° C. for 2 h. The result obtained in this way is a zeolite Z2d of structural type MFS, which is not dealuminated, and comprising an amorphous silica layer on its external and internal surfaces.

The zeolite Z2d is then shaped by extrusion with an alumina gel so as to produce after drying at 120° C. and calcination at 450° C. in dry air, a catalyst which contains 60% by weight of zeolite Z2d and 40% by weight of alumina.

Example 6 (Comparative)

Treatment of a Zeolite of Structural Type MOR Without a Dealumination Step

The same treatment as that set forth in example 3 is carried out, with omission of the dealumination step.

An amount of 100 g of zeolite H-MOR (Si/Al=9.1) was exchanged using a solution of $NH_4NO_3$ under reflux for a period of 2 h, and then dried. After activation of the exchanged zeolite in a flow of nitrogen in a fixed bed reactor at 200° C. the temperature of the reactor is adjusted to 50° C. and then a partial pressure of 0.15 bar of $Si_2H_6$ is added in the flow of nitrogen. After 2 h of reaction the zeolite is stripped for 24 h at 120° C. to evacuate the non-reactive $Si_2H_6$. Decomposition of the molecular compound $Si_2H_6$ is effected in $N_2$ saturated in respect of $H_2O$ at 350° C. for 2 h, then a heat treatment in pure $N_2$ is effected at 450° C. for 2 h. The result obtained in this way is a zeolite Z3d of structural type MOR, which is not dealuminated, and comprising an amorphous silica layer on its external and internal surfaces.

The zeolite Z3d is then shaped by extrusion with an alumina gel so as to produce after drying at 120° C. and calcination at 450° C. in dry air, a catalyst which contains 60% by weight of zeolite Z3d and 40% by weight of alumina.

Example 7 (Comparative)

Treatment of a Zeolite of Structural Type FER Without the Cationic Exchange Step The same treatment as that set forth in example 1 is carried out, with omission of the cationic exchange step prior to the treatment step in the presence of the molecular compound $Si_2H_6$.

An amount of 100 g of zeolite H-FER (Si/Al=10.2) was treated for 2 hours at 600° C. in a flow of $N_2$ containing 60% by weight of $H_2O$. The resulting zeolite is then treated twice using an aqueous solution of acid $HNO_3$ at a concentration of ION (volume solution/volume zeolite=5) under reflux for 3 hours, washed twice with distilled water and then dried. After activation of the dealuminated zeolite in a flow of nitrogen in a fixed bed reactor at 200° C. the temperature of the reactor is adjusted to 50° C. and then a partial pressure of 0.15 bar of $Si_2H_6$ is added in the flow of nitrogen. After 2 h of reaction the zeolite is stripped for 24 h at 120° C. to evacuate the non-reactive $Si_2H_6$. Decomposition of the molecular compound $Si_2H_6$ is effected in $N_2$ saturated in respect of $H_2O$ at 350° C. for 2 h, then a heat treatment in pure $N_2$ is effected at 450° C. for 2 h. The result obtained in this way is a zeolite Z1e of structural type FER comprising an amorphous silica layer on its external and internal surfaces.

The zeolite Z1e is then shaped by extrusion with an alumina gel so as to produce after drying at 120° C. and calcination at 450° C. in dry air, a catalyst which contains 60% by weight of zeolite Z1e and 40% by weight of alumina.

Example 8 (Comparative)

Treatment of a Zeolite of Structural Type MFS Without the Cationic Exchange Step The same treatment as that set forth in example 2 is carried out, with omission of the cationic exchange step prior to the treatment step in the presence of the molecular compound $Si_2H_6$.

An amount of 20 g of zeolite Na-ZSM-57 (Si/Al=45.2) was treated for 2 hours at 600° C. in a flow of $N_2$ containing 60% by weight of $H_2O$. The resulting zeolite is then treated twice using an aqueous solution of acid $HNO_3$ at a concentration of 10N (volume solution/volume zeolite=5) under reflux for 3 hours, washed twice with distilled water and then dried. After activation of the dealuminated zeolite in a flow of nitrogen in a fixed bed reactor at 450° C. the temperature of the reactor is adjusted to 50° C. and then a partial pressure of 0.15 bar of $Si_2H_6$ is added in the flow of nitrogen. After 2 h of reaction the zeolite is stripped for 24 h at 120° C. to evacuate the non-reactive $Si_2H_6$. Decomposition of the molecular compound $Si_2H_6$ is effected in $N_2$ saturated in respect of $H_2O$ at 350° C. for 2 h. Finally the zeolite is exchanged using a solution of $NH_4NO_3$ under reflux for 2 hours and then calcined at 450° C. for 2 hours. The result obtained in this way is a zeolite Z2e of structural type MFS comprising an amorphous silica layer on its external and internal surfaces.

The zeolite Z2e is then shaped by extrusion with an alumina gel so as to produce after drying at 120° C. and calcination at 450° C. in dry air, a catalyst which contains 60% by weight of zeolite Z2e and 40% by weight of alumina.

Example 9 (Comparative)

Treatment of a Zeolite of Structural Type MOR Without the Cationic Exchange Step The same treatment as that set forth in example 3 is carried out, with omission of the cationic exchange step prior to the treatment step in the presence of the molecular compound $Si_2H_6$.

An amount of 100 g of zeolite H-MOR (Si/Al=9.1) was treated for 2 hours at 650° C. in a flow of $N_2$ containing 60% by weight of $H_2O$. The resulting zeolite is then treated twice using an aqueous solution of acid $HNO_3$ at a concentration of 8N (volume solution/volume zeolite=5) under reflux for 3 hours, washed twice with distilled water and then dried. After activation of the dealuminated zeolite in a flow of nitrogen in a fixed bed reactor at 200° C. the temperature of the reactor is adjusted to 50° C. and then a partial pressure of 0.15 bar of $Si_2H_6$ is added in the flow of nitrogen. After 2 h of reaction the zeolite is stripped for 24 h at 120° C. to evacuate the non-reactive $Si_2H_6$. Decomposition of the molecular compound $Si_2H_6$ is effected in $N_2$ saturated in respect of $H_2O$ at 350° C. for 2 h, then a heat treatment in pure $N_2$ is effected at 450° C. for 2 h. The result obtained in this way is a zeolite Z3e of structural type MOR comprising an amorphous silica layer on its external and internal surfaces.

The zeolite Z3e is then shaped by extrusion with an alumina gel so as to produce after drying at 120° C. and calcination at 450° C. in dry air, a catalyst which contains 60% by weight of zeolite Z3e and 40% by weight of alumina.

Example 10

Evaluation of the Catalytic Properties of Different Catalysts in the Oligomerisation of Light Olefins The performances of the catalysts prepared in accordance with Examples 1 to 9 hereinbefore were evaluated in regard to oligomerisation of a light olefinic cut containing 54% of butenes and 4% of isobutene in a mixture of paraffins.

The operating conditions of the tests are as follows:
Temperature: 230° C.
Pressure: 6 MPa
VVH ($h^{-1}$) [volume of catalyst/flow by volume of charge]: 1 $h^{-1}$ The catalysts are previously activated in situ in $N_2$ at 450° C. for a period of 2 h.

The performances of the catalysts based on zeolite of structural type FER are set forth in Table 1.

TABLE 1

Performances of catalysts based on the zeolite FER

| | Z1-based catalyst | Z1d-based catalyst | Z1e-based catalyst |
|---|---|---|---|
| Olefinic C4 conversion (%) | 69 | 27 | 3 |
| Yield petrol cut (%) | 31 | 11 | <2% |
| Yield diesel cut (%) | 29 | 4 | — |
| Cetane number | 47 | 35 | — |

The performances of the catalysts based on the zeolite ZSM-57 of structural type MFS are set forth in Table 2.

TABLE 2

Performances of catalysts based on the zeolite ZSM-57

| | Z2-based catalyst | Z2d-based catalyst | Z2e-based catalyst |
|---|---|---|---|
| Olefinic C4 conversion (%) | 72 | 32 | 67 |
| Yield petrol cut (%) | 33 | 13 | 31 |
| Yield diesel cut (%) | 31 | 2 | 26 |
| Cetane number | 48 | — | 47 |

The performances of the catalysts based on the zeolite of structural type MOR are set forth in Table 3.

TABLE 3

Performances of catalysts based on the zeolite MOR

| | Z3-based catalyst | Z3d-based catalyst | Z3e-based catalyst |
|---|---|---|---|
| Olefinic C4 conversion (%) | 99 | 31 | <2 |
| Yield petrol cut (%) | 38 | 10 | — |
| Yield diesel cut (%) | 57 | 6 | — |
| Cetane number | 41 | 33 | — |

The catalytic performances set forth in Tables 1, 2 and 3 demonstrate that the catalyst comprising a zeolite which is modified and prepared in accordance with the treatment process of the invention makes it possible to noticeably enhance the activity of the catalyst for olefinic C4 conversion, thus enhancing the yields in respect of petrol and diesel cuts. The quality of that gas oil measured by its cetane number (CI) is thus improved in relation to that afforded by a diesel cut obtained by means of a catalyst comprising a zeolite which has not been treated in accordance with the treatment process of the invention. It is clear that the dealumination and cationic exchange steps are essential in the treatment process according to the invention.

The invention claimed is:
1. A process comprising conducting catalytic oligomerisation of an olefinic charge containing hydrocarbon molecules having from 2 to 12 carbon atoms per molecule, the improvement wherein the catalyst is a shaped catalyst comprising at least one zeolite having a pore size of less than or equal to 7 Å and a matrix incorporating said zeolite having been subjected to at least the following successive steps:
   a) dealumination of said zeolite,
   b) cationic exchange with at least one cation selected from the group consisting of ammonium cation and cations of metals of groups IA and IIA of the periodic table,
   c) treatment of cation-exchanged zeolite obtained in b) in the presence of at least one molecular compound containing at least one silicon atom, and
   d) at least one heat treatment.

2. A process according to claim 1 wherein said zeolite initially has an Si/Al atomic ratio of between 2 and 200.

3. A process according to claim 1 wherein said zeolite is selected from the zeolites of structural type MEL, MFI, ITH, NES, EUO, ERI, FER, CHA, MFS, MWW, MTT, TON and MOR.

4. A process according to claim 1 wherein said zeolite, prior to implementation of a), is in calcined form and contains at least one cation.

5. A process according to claim 1 wherein said molecular compound containing at least one silicon atom is selected from the compounds of the formulae $S_1$—$R_4$ and $Si_2$—$R_6$ wherein R can be either hydrogen or an alkyl, aryl or acyl group, or an alkoxy group (O—R') or a hydroxyl group (—OH) or a halogen.

6. A process according to claim 1 wherein said molecular compound containing at least one silicon atom is a silane, disilane, alkylsilane, alkoxysilane or siloxane.

7. A process according to claim 1 wherein c) is implemented by effecting the deposit of said molecular compound comprising at least one silicon atom in a gaseous phase.

8. A process according to claim 7 wherein c) is implemented in a fixed bed reactor.

9. A process according to claim 1 wherein d) is followed by e) exchange of said cation by an ammonium cation, itself followed by f) consisting of a heat treatment.

10. A process according to claim 1 wherein said charge contains from 25 to 80% by weight of olefins, wherein linear olefins represent 15 to 95% by weight of all of the olefins present in said charge.

11. A process according to claim 1 wherein said oligomerisation process is carried out at a temperature of between 40 and 600° C., with a total pressure of between 0.1 and 10 MPa and a spatial hourly velocity (VVH) of between 0.01 and 100 $h^{-1}$.

12. A process according to claim 1 where the at least one cation is selected from the group consisting of $Na^+$, $Li^+$, $K^+$, $Rb^+$, $Cs^+$, $Ba^{2+}$ and $Ca^{2+}$.

13. A process according to claim 1 wherein said at least one cation other than $H^+$ is an ammonium ion.

14. A process according to claim 1 wherein the exchange zeolite produced in b) is devoid of any H+ cation.

15. A process according to claim 1 wherein said olefinic charge contains molecules having four carbon atoms per molecule.

16. A process according to claim 1 wherein said olefinic charge contains a major amount of molecules having four carbon atoms per molecule.

17. A process according to claim 16 wherein said zeolite is an MOR zeolite.

18. A process according to claim 1 wherein said zeolite is an MOR zeolite.

* * * * *

UNITED STATES PATENT AND TRADEMARK OFFICE
CERTIFICATE OF CORRECTION

PATENT NO.         : 8,598,397 B2                                    Page 1 of 1
APPLICATION NO.    : 11/993996
DATED              : December 3, 2013
INVENTOR(S)        : Simon et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1283 days.

Signed and Sealed this
Twenty-second Day of September, 2015

Michelle K. Lee
*Director of the United States Patent and Trademark Office*